United States Patent [19]

Asatiani et al.

[11] Patent Number: 4,695,360
[45] Date of Patent: Sep. 22, 1987

[54] DEVICE FOR ELECTROCHEMICAL-ETCHING DETERMINATION OF CORROSION RESISTANCE OF METALS

[75] Inventors: Georgy N. Asatiani; Evgeny A. Pikus; Elgudzha R. Kutelia; David M. Tsivtsivadze; Yason N. Mudzhiri; Nikolai V. Dzhalabadze, all of Tbilisi, U.S.S.R.

[73] Assignee: Gruzinsky Politekhnichesky Institute, Tbilisi, U.S.S.R.

[21] Appl. No.: 805,800

[22] Filed: Dec. 6, 1985

[30] Foreign Application Priority Data

Dec. 6, 1984 [SU] U.S.S.R. ............................ 3820850

[51] Int. Cl.[4] .......................................... G01N 27/46
[52] U.S. Cl. ................................. 204/404; 204/1 T; 204/400; 204/435; 204/129.2
[58] Field of Search ............ 204/1 T, 1 C, 400, 404, 204/435, 129.2

[56] References Cited

U.S. PATENT DOCUMENTS

| | | | |
|---|---|---|---|
| 3,492,860 | 2/1970 | Bailey | 204/404 |
| 4,006,063 | 2/1977 | Ensanian | 204/1 T |
| 4,019,129 | 4/1977 | Grau | 204/434 |
| 4,240,892 | 12/1980 | Riggs | 204/404 |

OTHER PUBLICATIONS

Evans, "Metallic Corrosion Passivity & Protection", 1948, pp. 21 & 22.

Primary Examiner—T Tung
Attorney, Agent, or Firm—Fleit, Jacobson, Cohn & Price

[57] ABSTRACT

The device comprises an electrochemical cell with polarization electrodes, a sample holder, a reference electrode with a capillary probe, a potential meter and a power supply source. The sample holder is mounted so that when a test sample is placed thereinto, the working surface of the sample is positioned perpendicular to the surfaces of the polarization electrodes. The polarization electrodes and the capillary probe are movably mounted.

9 Claims, 2 Drawing Figures

DEVICE FOR ELECTROCHEMICAL-ETCHING DETERMINATION OF CORROSION RESISTANCE OF METALS

FIELD OF THE INVENTION

The present invention relates to the technology of measurement and, more specifically, to devices for the determination of corrosion resistance of metals by way of an electrochemical etching.

The present invention can be successfully used in those industries where corrosion-resistant materials are employed or where it is necessary to identify the structural state of steels and alloys, for example in chemical industry, metallurgy, petrochemical industry, as well as in research and educational-and-methodological work.

In recent years in the art of corrosion control electrochemical methods and devices find an ever-growing application for the determination of corrosion resistance of metals and alloys. It has been found that the decisive role in processes of passivation and depassivation of metals is played by the electrode potential value.

The majority of local types of corrosion, such as anodic dissolution, passivation, cathodic dissolution, intercrystallite corrosion, transpassivation, pitting corrosion are, in their nature, electrochemical processes.

Known in the art is a device for the determination of resistance of metals to pitting corrosion by way of electrochemical etching.

The device comprises an electrochemical cell, a DC source with its terminals being connected to a specimen of the test metal placed into an electrolyte and an auxiliary electrode (cf. paper by Waard G., Nicholson J. W., Posch W. in Journal "Werkstoff und Korrosion", 1968, 19, Nr. 9, s. 782–785).

In the known device a voltage drop occurs inside the specimen itself which is of 1 m in length and 1.5 mm in diameter. In this case a very narrow range of variations of potential is obtained, since for a higher voltage drop along the specimen it is necessary to either increase the specimen length or to raise the current supplied from the power source (which, however, causes heating of the specimen, electrolyte and changes the conditions of the experiment).

A small range of the potential variations along the specimen length makes it possible to determine, by means of the known device, the resistance of metal to only one type of corrosion; besides, the device is cumbersome, difficult to maintain and operate.

Also known is a device for the electrochemical-etching determination of corrosion resistance of metals, which comprises an electrochemical cell with two polarizing electrodes, a holder for the specimen of the test metal placed therebetween, a reference electrode with a capillary probe intended for contacting the working surface of the test specimen, an electric contact with a lead provided in the holder and intended for interacting with the specimen when the latter is placed into the holder; a potential meter connected between the reference electrode and the lead of the electric contact and a power supply source with its terminals connected to the polarizing electron (see in G. V. Akimov, "Theory and Methods of Investigation of Metal Corrosion", Moscow-Leningrad, USSR Academy of Sciences Publishing House, 1945, p. 358–359). In this device the holder ensures a vertical position of a sample, i.e. such position in which the working surface of the sample is parallel to the opposite surfaces of the polarizing electrodes (perpendicular to the lines of force of the polarization field). In the known device the capillary probe is embodied as a stationary glass tubule.

The known device makes it possible in one experiment to reproduce on the surface of the test sample only one kind of corrosion which is defined by the sample position relative to the polarization electrodes and the position of the stationary tubule of the reference electrode relative to the sample.

To determine the resistance of the test metal to other types of corrosion, it is necessary to use a new sample of metal for each new experiment, which is associated with high consumption of materials, power, and time.

SUMMARY OF THE INVENTION

It is an object of the present invention to reduce the time required for the determination of corrosion resistance of metals by way of electrochemical etching.

It is another object of the present invention to ensure the possibility of the device operation under both manual and automatic control.

It is still another object of the present invention to make the work with the device and its maintenance more convenient.

These objects are accomplished by that in a device for an electrochemical-etching determination of corrosion resistance of metals comprising an electrochemical cell with two polarization electrodes, a holder for a sample of the test metal positioned therebetween, a reference electrode with a capillary probe intended for interaction with the working surface of the sample, an electric contact with a lead mounted in the holder and adapted for interaction with the sample when the latter is placed into the holder, a potential meter connected to the reference electrode and to the lead of the electric contact, and a power supply source with its terminals being connected to the polarization electrodes, in accordance with the present invention, the sample holder is positioned in the cell so that upon placing the test sample thereinto the working surface of the sample becomes positioned perpendicular to the opposite surface of the polarization electrodes; the capillary probe of the reference electrode being mounted movably in a direction perpendicular to the opposite surface of the polarizing electrodes.

It is advisable, for ensuring the possibility of variation the scale of the potential range realized along the entire length of the sample surface, to place the polarization electrodes in the electrochemical cell in such a manner as to provide an opportunity for varying the distance between these electrodes.

In order to ensure functioning of the device under automatic operation conditions, it is advisable to provide it with an electric motor for moving the capillary probe with its output shaft being coupled to a convertor of the capillary probe movement into electric pulses connected with its output to a pulse counter which, in turn, is connected with its output to series-connected transcriptor and numerical printer and, through its output and a first D/A convertor to the input "X" of an X-Y plotter, with an electric motor for moving the polarization electrodes, a unit of multi-position switches connected with one output thereof to the electric motor for moving the polarization electrodes and with the other output to the input of the power supply source of the electric motor for moving the capillary probe and, with its third output—to the monitoring input of the power supply source of the polarization electrodes, a second D/A convertor connected with its input to the output of a digital potential meter and to the input of the transcriptor and, with its output, to the output "Y" of the X-Y plotter.

The device for the determination of corrosion resistance of metals by way of an electrochemical etching according to the present invention makes it possible to obtain, in the same experiment on the surface of the same sample of a test metal, a spectrum of regions etched at different potentials corresponding to diverse electrochemical processes. The device is convenient in maintenance, it can be operated both manually and automatically, it is noted for its simple design.

BRIEF DESCRIPTION OF DRAWINGS

The present invention is further illustrated by the description of a particular embodiment thereof with reference to the accompanying drawings, wherein.

Figure 1:
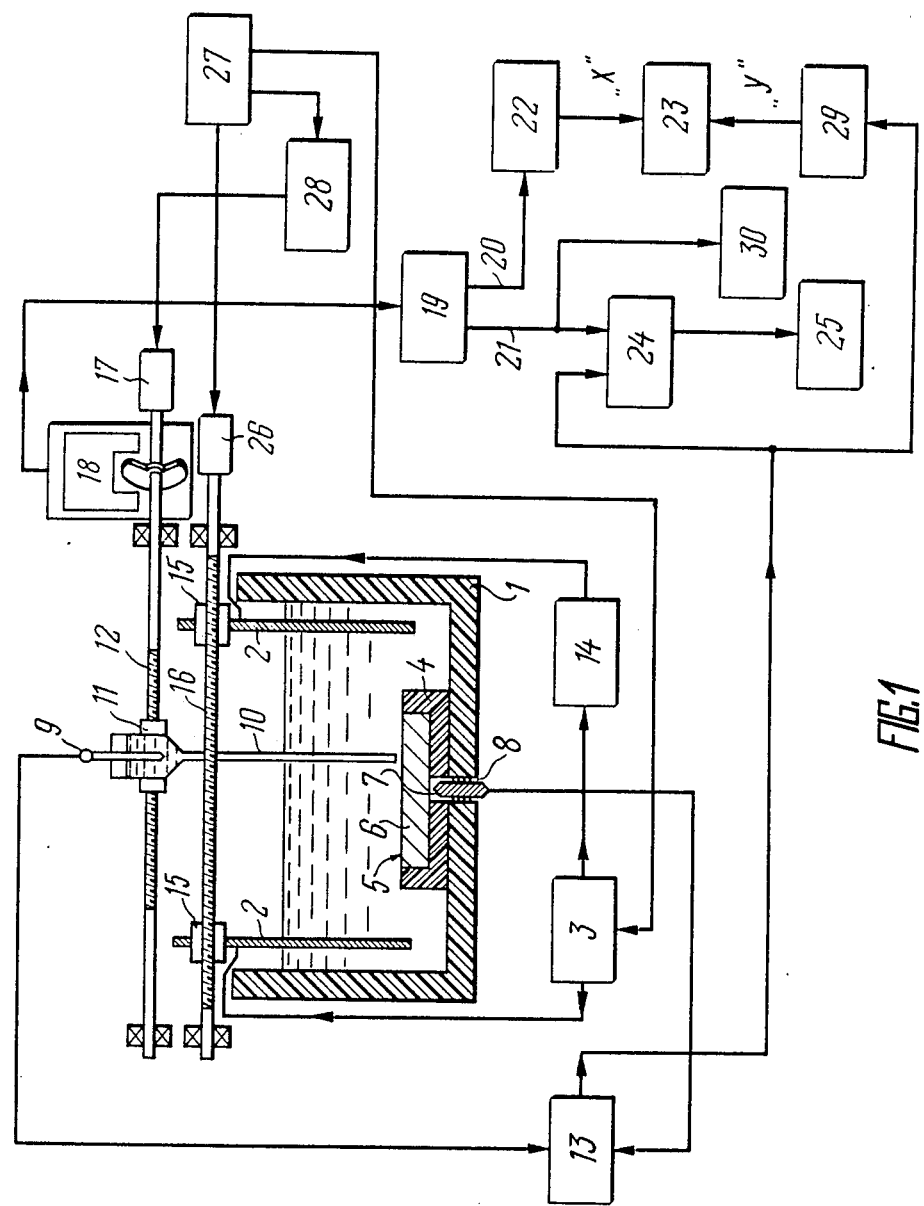
FIG. 1 is a schematic diagram of the device for the electrochemical-etching determination of corrosion resistance of metals.

The device for the electrochemical-etching determination of corrosion resistance of metals as shown in FIG. 1 comprises an electrochemical cell 1 with an electrolyte, wherein vertically and parallel to one another two plate-type polarization electrodes 2 are mounted, each being connected to a respective terminal of an adjustable power supply source 3. A holder 4 is positioned between the electrodes 2 in the cell 1 so that the working surface 5 (interacting with the electrolyte) of a sample 6 positioned in its socket is horizontal and perpendicular to the opposite surfaces of the polarization electrodes 2. Into the holder 4 made from an electroinsulating material an electric contact is mounted having a lead 8 and contacting with the surface of the sample 6 protected from the action of the electrolyte. Furthermore, the device comprises a reference electrode 9 with a capillary probe 10 contecting with its free end the working surface 5 of the sample 6. The capillary probe 10 is mounted with the possibility of moving along the working surface 5 in a direction perpendicular to the opposite surfaces of the polarization electrodes 2 by means of a worm pair 11-12. A potential meter 13 made as a digital voltmeter is interconnected between the reference electrode 9 and the lead 8. In the power supply circuit of the polarization electrodes 2 a limiter 14 of the current passing through the electrolyte is provided. The polarization electrodes in the embodiment being described are mounted with the possibility of changing the distance therebetween, wherefore each of them is rigidly secured with a respective nut 15 engaged with a worm 16.

The device for the determination of corrosion resistance of metals according to the present invention also incorporates an electric motor 17 for moving the capillary probe 10 with its output shaft being coupled, by means of a friction gear (not shown) to the worm pair 11-12, a convertor 18 of the capillary probe 10 movement into electric pulses coupled with the output shaft of a motor 17 and connected with its output to a pulse counter 19 having two outputs 20 and 21, at one of which a binary code is formed and this output 20 is connected, through a digital-to-analog convertor 22, to the input "X" of an X-Y plotter 23, while at the other output a binary-decimal code is formed and this output 21 is connected to series-connected transcriptor 24 (a convertor of the binary-decimal code into the monitoring code of unit 25) and a numerical printer 25. The device according to the present invention also comprises an electric motor 26 for moving the polarization electrodes 2 with its output shaft being coupled by means of a friction gear (not shown) to the worm 16, a unit of multi-position switches 27 connected with one output to the electric motor 26 and with another output—to the input of an adjustable power supply unit 28 of the electric motor 17, and with its third output, to the monitoring input of the power source 3 of the polarization electrodes 2, and a D/A convertor 29 with its input connected to the output of the potential meter 13, while the convertor's output is connected, in turn, to the input "Y" of the X-Y plotter 23. Furthermore, the output of the potential meter 13 is connected to the second input of the transcriptor 24, while the output 21 of the pulse counter 19 is connected to a display 30.

Figure 2:
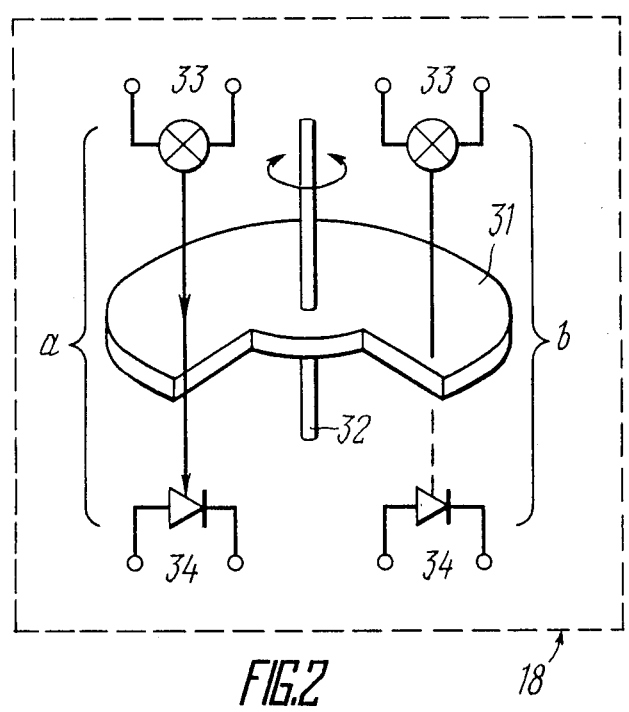
FIG. 2 is a schematic diagram of the convertor of the capillary probe movement into electric pulses.

As the convertor 18 of the capillary probe 10 converts movement into electric pulses, use is made of a photoelectronic transducer schematically shown in FIG. 2. The convertor 18 has a disc 31 with an orifice 32, which disc is non-transparent for light radiation, rigidly secured on the shaft of the electric motor for moving the capillary probe, and two optical pairs "a" and "b" each consisting of a light source 33 and a photodiode 34.

The device for the determination of corrosion resistance of metals according to the present invention operates in the following manner.

The sample 6 of the test metal prepared on the side of its flat surface as a metallographic microsection is pressed into the socket of the holder 4; in doing so, its surface opposite to the working surface 5 interacts with the electric contact 7. The capillary probe 10 is set at the edge of the sample 6. The switches of the unit 27 are set in position defining the desired speed of movement of the capillary probe 10 (by setting the base voltage for the supply source 28), the polarization volt value (by setting the base voltage for the supp source 3 and the supply and polarity for the electric motor 26), the number of points of measurement of potentials (by setting the measurement frequency for the potential meter 13).

After the command "ON" the device operates automatically.

The required difference of potentials between the electodes 2 (spectrum of potentials) is preset by the voltage in the power supply source 3 and by the position of the polarization electrodes (the distance therebetween). The value of the current passing through the electrolyte is controlled and, if necessary, limited by the current limiter 14 (e.g. electronic switch).

The measurement of potentials on the surface 5 of the sample 6 is effected by means of the capillary probe 10 with the reference electrode 9 which is moved by means of the electric motor 17 along the working surface 5 of the sample 6. The position of the capillary probe is recorded by means of the photoelectronic convertor 18, wherein the number of revolutions of the disc 31 (FIG. 2) is transformed into pulses the number of which provides information on the movement of the capillary probe 10.

Depending on the direction of rotation of the electric motor, the photodiode of the optical pair "a" or "b" lights up first.

The electronic circuit of the pulse counter 19 decodes the sequence of pulses coming from the photodiodes 34 and determines the direction of rotation of the shaft and, hence, of the movement of the capillary probe 10. The number of pulses defines the distance passed by the capillary probe 10. In the present embodiment of the device the mechanical gear is made so that the path of 1 mm corresponds to 10 revolutions of the shaft of the electric motor, i.e. the resolving power is equal to 0.1 mm/pulse.

The potential is measured by means of an electronic digital potential meter 13—voltmeter. Information is delivered through the transcriptor 24 to the numerical printer 25, to the display 30 and to the input "X" of the X-Y plotter 23.

After covering by the capillary probe 10 the entire length of the sample the measurement is discontinued, the capillary probe is returned to the starting position and the device is again ready for operation.

When a more detailed investigation of the electrochemical behaviour of the test metal in the cathodic active or passive region is required, use is made of the movement (by means of the electric motor 26 and the worm pair 15-16) of the polarization electrodes 2 or one of them along the lines of force of the polarization field, thereby ensuring a greater scale and shift of the potential spectrum towards the selected region.

It should be noted that the device according to the present invention ensures realization, in the zone of location of the test sample in the electrolyte of a potential spectrum from given positive values of potential to negative ones with passing through the "zero" potential in one experiment. This makes it possible to simulate, on the sample surface, substantially all electrochemical regions and to analyze the corrosion resistance of a metal in a given electrolyte using only one sample in a single experiment.

By means of the device according to the present invention the surface of a steel containing 0.003% of C, 18% of Cr, 20% of Ni, 2% of Mo and 1% of Si was studied.

A sample of this steel with the length of 5 cm prepared as a metallographic microsection was placed into the socket of the holder 4 of the device and an electrolyte, i.e. 5% sulphuric acid was poured into the cell 1. The spectrum of variation of potentials between the polarization electrodes 2 was selected within the range of from −1.15 to +1.15 V. The measurement of the potential was effected in 50 points along the sample length. The measurement process took about 5 minutes. The comparison of the relationship of the distribution of potentials along the surface of the sample with the potentiodynamic curve gave an opportunity of determining the regions etched at various values of the potential spectrum which was clearly seen in the metallographic scanned picture (OM) (cathodic region, active region, passive region).

Morphological (REM) and micro-X-ray spectroscobic (XRMA) studies have shown, in particular, the presence of centers of preferable dissolution and their distribution over electrochemical regions.

REFERENCE CHARACTERS

3—power supply source,
13—potential meter,
14—current limiter,
17—electric motor,
18—convertor of motion into electric pulses,
19—pulse counter,
22—digital-to-analog convertor,
23—X-Y plotter,
24—transcriptor,
25—figure-printing unit,
26—electric motor,
27—unit of multi-position switches,
28—power supply unit,
29—digital-to-analog convertor,
30—display.

What is claimed is:

1. A device for an electrochemical-etching determination of corrosion resistance of metals comprising:
   an electrochemical cell including an electrolyte;
   first and second polarization electrodes mounted spaced apart in said electrochemical cell, presenting opposing surfaces facing each other;
   power supply means with its output electrically connected to said polarization electrodes;
   a holder for a sample of a test metal to be tested in said cell, said holder being located between polarization electrodes and being mounted in said electrochemical cell so that when the test sample is placed thereinto the working surface of said test sample interacting with the electrolyte lies in a position perpendicular to said opposing surfaces of the polarization electrodes;
   electric contact means located in said holder for contact with a sample placed therein, and extending to the exterior of the electrochemical cell;
   reference electrode means including a capillary probe mounted in said electrochemical cell with said capillary probe terminating adjacent the working surface of the test sample when placed in said holder;
   movement means for said reference electrode means to move said capillary probe in a direction perpendicular to said opposing surfaces of the polarization electrodes and along the working surface of said test sample to interact therewith; and
   potential meter means interconnected, between said reference electrode means and said electric contact means to generate a signal indicative of the potential difference therebetween.

2. A device as claimed in claim 1, wherein drive means are provided to move said polarization electrodes toward and away from each other to change the distance between them and their positions relative to a test sample placed in said holder.

3. A device as claimed in claim 2 wherein said drive means and said movement means include electric motors.

4. A device as claimed in claim 1 including a converter means coacting with said movement means to generate signals responsive to the movement of the capillary probe and display means for receiving said signals from said converter means and signals from said potential meter means and for displaying an output correlated with the position of the capillary probe and the potential difference between the capillary probe and the electric contact means.

5. A device as claimed in claim 4 including drive means to move said polarization electrodes toward and away from each other to change the distance between them.

6. A device as claimed in claim 4 wherein said display means includes an X-Y plotter.

7. A device as claimed in claim 4 wherein said display means includes a numerical printer.

8. A device as claimed in claim 4 wherein said converter means includes digital means for generating digital signals and a converter to convert same to analog signals.

9. A device as claimed in claim 8 wherein said display means includes a visual display of the generated digital signals.

* * * * *